US010368925B2

(12) United States Patent
Steffensmeier et al.

(10) Patent No.: US 10,368,925 B2
(45) Date of Patent: Aug. 6, 2019

(54) ALIGNMENT DEVICES AND METHODS

(71) Applicant: Jace Medical, LLC, Winona Lake, IN (US)

(72) Inventors: Scott Steffensmeier, Winona Lake, IN (US); Jason F Detweiler, Warsaw, IN (US)

(73) Assignee: Jace Medical, LLC, Winona Lake, IN (US)

( * ) Notice: Subject to any disclaimer, the term of this patent is extended or adjusted under 35 U.S.C. 154(b) by 262 days.

(21) Appl. No.: 15/265,143

(22) Filed: Sep. 14, 2016

(65) Prior Publication Data
US 2017/0071644 A1    Mar. 16, 2017

Related U.S. Application Data

(60) Provisional application No. 62/218,943, filed on Sep. 15, 2015.

(51) Int. Cl.
*A61B 17/80* (2006.01)
*A61B 17/68* (2006.01)

(52) U.S. Cl.
CPC .......... *A61B 17/8004* (2013.01); *A61B 17/68* (2013.01); *A61B 17/8023* (2013.01); *A61B 17/8061* (2013.01); *A61B 2017/681* (2013.01)

(58) Field of Classification Search
CPC ............ A61B 17/8076; A61B 17/1789; A61B 17/808
See application file for complete search history.

(56) References Cited

U.S. PATENT DOCUMENTS

| 5,423,826 A * | 6/1995 | Coates ............... A61B 17/1728 606/281 |
| 9,408,720 B2 * | 8/2016 | Krebs ..................... A61F 2/461 |
| 2005/0113831 A1 | 5/2005 | Franck et al. |
| 2006/0235398 A1 | 10/2006 | Farris et al. |
| 2011/0004254 A1 * | 1/2011 | Beger ................. A61B 17/1728 606/289 |
| 2011/0137353 A1 | 6/2011 | Buttermann |
| 2015/0119887 A1 | 4/2015 | May et al. |
| 2015/0209093 A1 * | 7/2015 | Dallis ................ A61B 17/8023 606/281 |

OTHER PUBLICATIONS

International Search Report for international application No. PCT/US16/51664, dated Dec. 2, 2016.

* cited by examiner

*Primary Examiner* — Andrew Yang
(74) *Attorney, Agent, or Firm* — Taylor IP, PC

(57) ABSTRACT

An alignment guide system is disclosed that includes a first alignment guide and a second alignment guide. The first and second alignment guides are adapted to couple to plates affixed to a bone or other body part and guide the plates together to close a resection or opening in the bone or other body part. The alignment guide system allows for an easy one person closure of the resection or opening in the bone or other body part.

18 Claims, 14 Drawing Sheets

ALIGNMENT DEVICES AND METHODS

CROSS REFERENCES TO RELATED APPLICATIONS

This application claims the benefit of U.S. Provisional Patent Application Ser. No. 62/218,943, entitled Alignment Devices and Methods, filed on Sep. 15, 2015, the contents of which are incorporated herein by reference in their entirety.

FIELD

The disclosure relates generally to alignment apparatuses and devices. More particularly, the disclosure relates to alignment apparatuses and devices for use in bone fixation, such as sternum fixation pre- or post-sternotomy, and other orthopaedic fixation procedures.

BACKGROUND

In some surgical procedures involving bones, for instance, the procedure may involve separating a bone into portions, which are thereafter reunited. This happens, for example, in entries into the chest cavity, as for heart surgery, where the sternum is required to be separated along its length. There may be other instances where a bone has undergone fracturing through some trauma, and is thereafter to have portions rejoined for proper healing. Additionally, in applications involving the spine, there may be independent bones that benefit from holding a particular position relative to each other to allow for healing of the disc and other surrounding tissues.

SUMMARY

An alignment guide system is disclosed that includes a first alignment guide and a second alignment guide. The first and second alignment guides are adapted to couple to plates affixed to a bone or other body part and guide the plates together to close a resection or opening in the bone or other body part. The alignment guide system allows for an easy one person/one handed closure of the resection or opening in the bone or other body part.

A system for guiding alignment of fixation devices may include a first alignment guide including a first retention mechanism adapted to couple the first alignment guide to a first fixation device on a first side of a cut body part. The system may also include a second alignment guide including a second retention mechanism adapted to couple the second alignment guide to a second fixation device on a second side of the cut body part, wherein the first and second alignment guides assist in aligning the first fixation device with the second fixation device to close the cut body part.

A device for guiding alignment of a fixation device may include a body portion, and a retention mechanism pivotably coupled to the body portion and adapted to couple the device to a first fixation device on a first side of a cut body part.

A device for guiding and aligning two pieces of a fixation device may include a first guide having a first pair of gripping elements movably coupled to the first guide and adapted to be movable between a first open position and a first closed position. In the first closed position, the first pair of gripping elements being adapted to releasably hold a first piece of the fixation device. The device may also include a second guide having a second pair of gripping elements movably coupled to the second guide and adapted to be movable between a second open position and a second closed position. In the second closed position, the second pair of gripping elements being adapted to releasably hold a second piece of the fixation device. The first and second guides may also be adapted to interconnect with one another to bring the first and second pieces of the fixation device into alignment.

BRIEF DESCRIPTION OF THE DRAWINGS

Embodiments of devices, systems, and methods are illustrated in the figures of the accompanying drawings which are meant to be exemplary and not limiting, in which like references are intended to refer to like or corresponding parts, and in which.

DETAILED DESCRIPTION

While the embodiments described hereinafter are in the environment of alignment devices, systems and methods for use in aligning orthopaedic fixation devices on the sternum with one another to correctly align separate bone portion, it should be appreciated that the disclosure has broader application, such as where bone or other calcaneus body parts require correct alignment.

Figure 1:
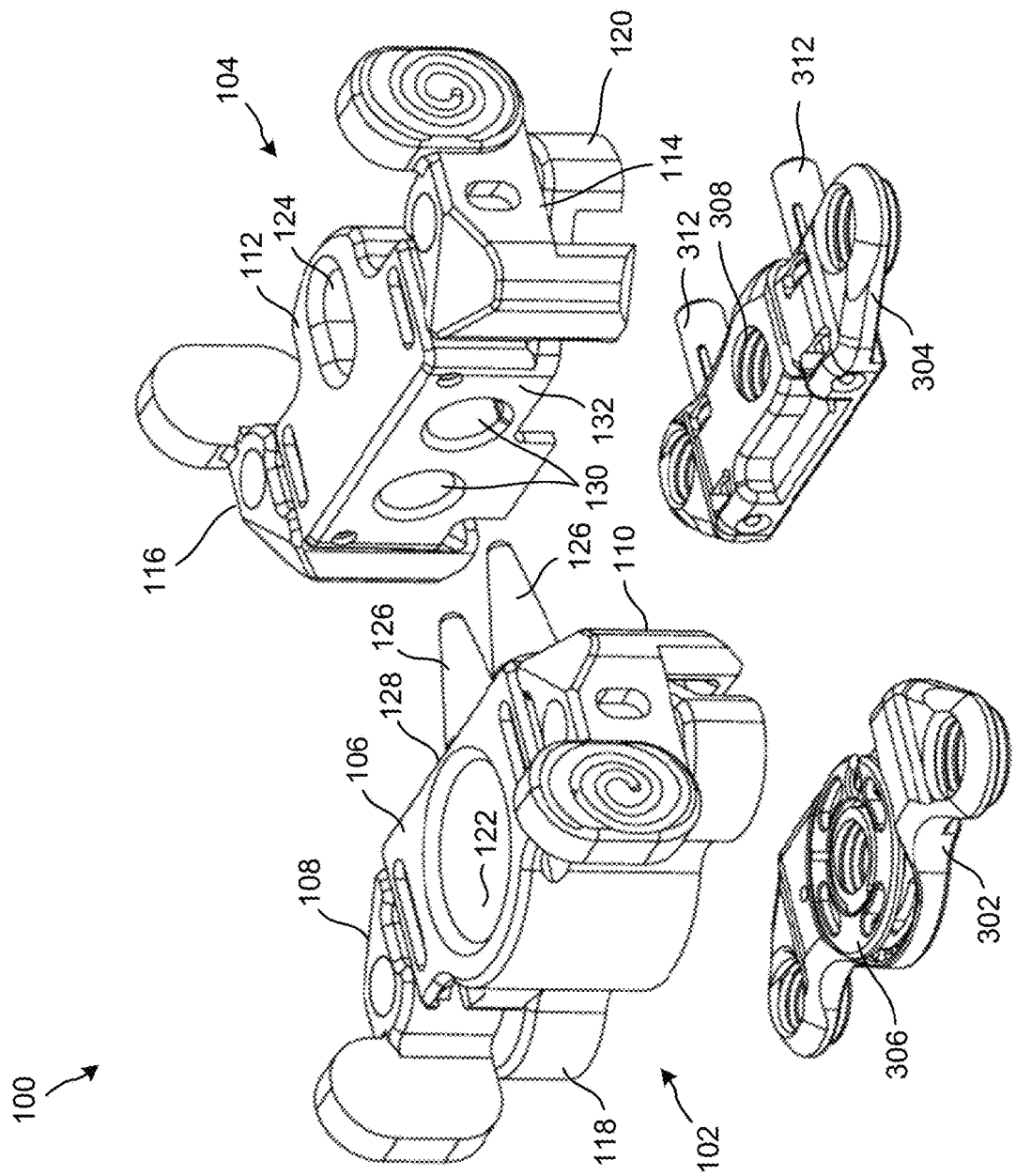
FIGS. 1 and 2 illustrate perspective views of alignment devices in accordance with an embodiment of the disclosure.
Figure 2:
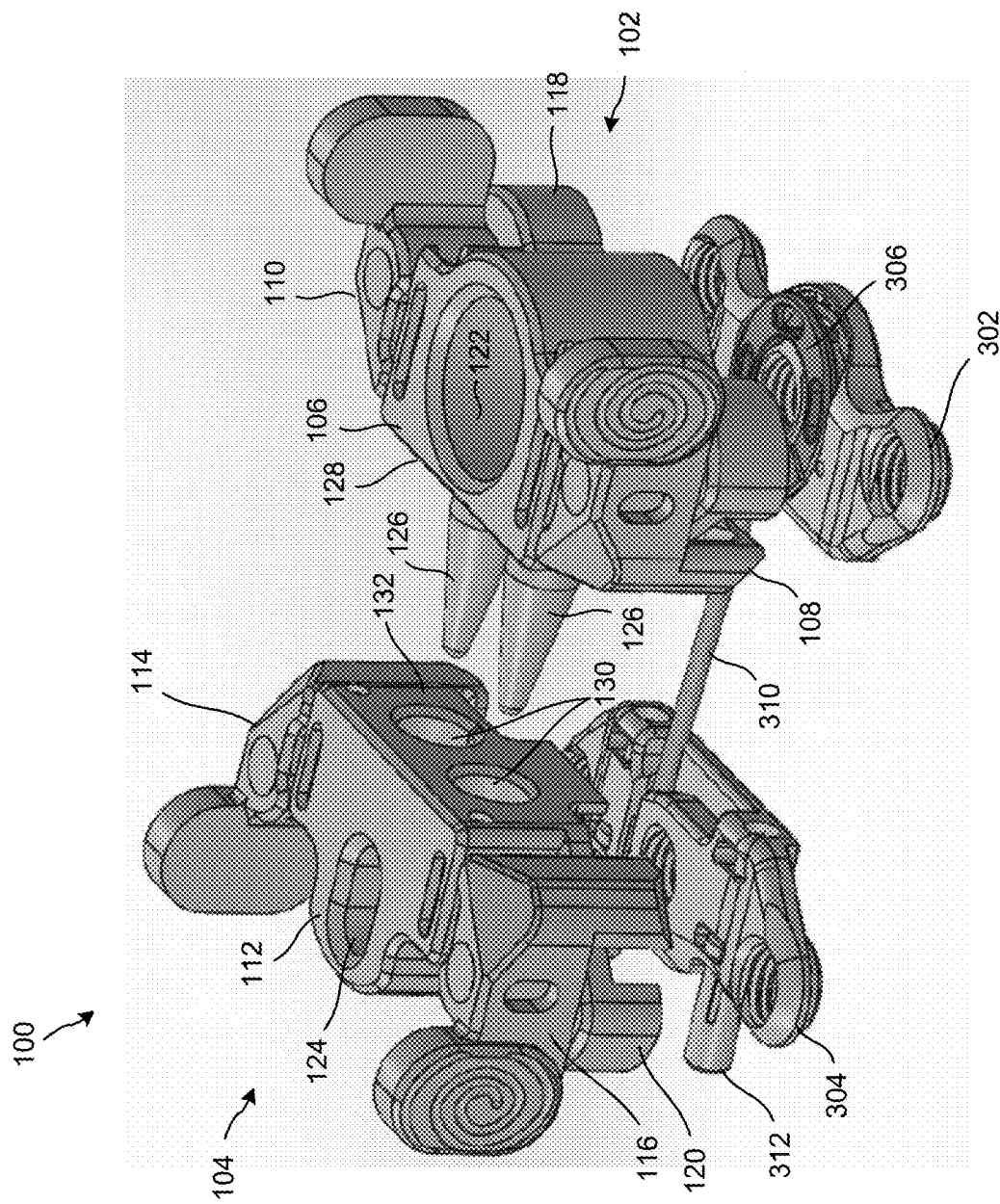

FIGS. 1 and 2 illustrate an alignment guide system 100, including a first alignment guide 102 and a second alignment guide 104. The first alignment guide 102 includes a first frame or body portion 106, a first plate retention mechanism 108 on a first side of the body portion 106, and a second plate retention mechanism 110 on a second side of the body portion 106 opposite the first side. Similarly, the second alignment guide 104 includes a second frame or body portion 112, a first plate retention mechanism 114 on a first side of the body portion 112, and a second plate retention mechanism 116 on a second side of the body portion 112 opposite the first side.

The first and second alignment guides 102 and 104 may be designed to receive and couple to plates, such as plates 302 and 304, respectively. The plates 302 and 304 may be the plates disclosed in U.S. Patent Application Publication No. 2015/0119887, entitled Orthopedic Fixation Device, System and Method, filed Oct. 27, 2014, the disclosure of which is incorporated by reference herein in its entirety.

For example, the first and second alignment guides 102 and 104 may include base portions 118 and 120, respectively, designed to receive and couple to the respective plates 302 and 304, as described in further detail below. In this respect, the first body portion 106 of the first alignment guide 102 may include a first aperture 122 extending substantially vertically through the first body portion 106. The first aperture 122 is positioned to align with a ratchet mechanism 306 of the plate 302. This allows for a tool to be inserted in the first aperture 122 and engaged with the ratchet mechanism 306. The first aperture 122 is also positioned to align with a fastener inserted or to be inserted in a fastener aperture of the plate 302. This allows for a tool, such as a tool adapted to engage the fastener, to be inserted in the first aperture 122 and engaged with the fastener for coupling or decoupling plate 302 to or from a bone.

Similarly, the second body portion 112 of the second alignment guide 104 may include a second aperture 124 extending substantially vertically through the second body portion 112. The second aperture 124 is positioned to align with a fastener inserted or to be inserted in a fastener aperture 308 of the plate 304. This allows for a tool, such as or a tool adapted to engage the fastener, to be inserted in the second aperture 124 and engaged with the fastener for coupling or decoupling plate 304 to or from a bone. The second aperture 124 also allows for a tool, such as a prying type tool, to be inserted in the second aperture to assist in controlling the orientation of the first and second alignment guides 102 and 104 with respect to each other. This may assist in drawing the plates 302 and 304, and by extension separated bone halves, together.

Figure 3:
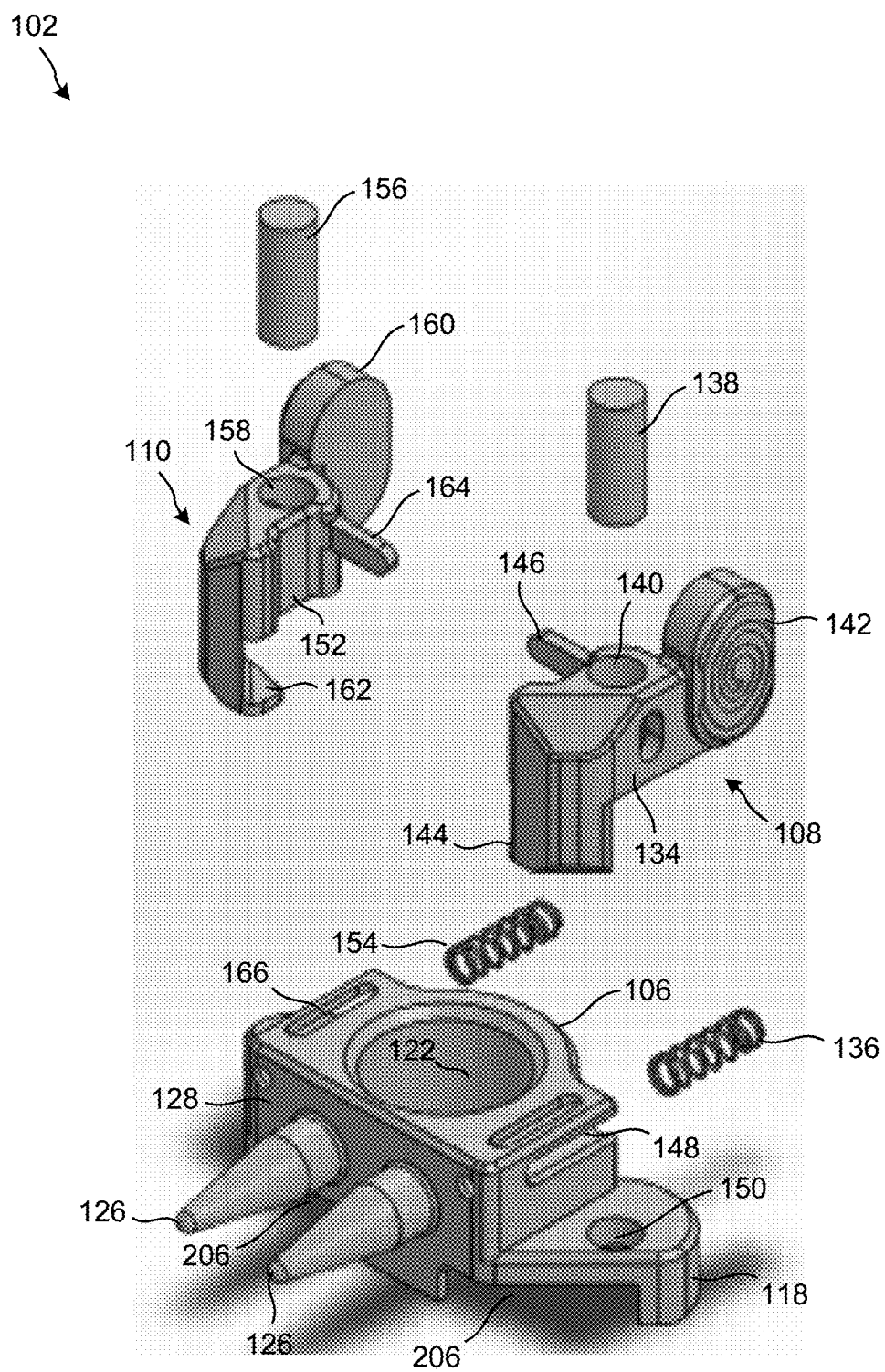
FIGS. 3 and 4 illustrate exploded views of the alignment devices of FIG. 1 in accordance with an embodiment of the disclosure.

The first body portion 106 may also include one or more protrusions 126 extending from a first face 128 (as best illustrated in FIG. 3) in a direction away from the first body portion 106/the first aperture 122. As illustrated, the protrusion(s) 126 may have a conical shape with a cross sectional area that decreases as the protrusion(s) 126 extend away from the first face 128. The second body portion 112 may also include one or more apertures 130 in a second face 132 extending into the second body portion 112. The aperture(s) 130 and the protrusion(s) 126 mate with one another to assist in aligning the plates 302 and 304 with one another as the plates 302 and 304 are drawn together. The conical shape of the protrusion(s) 126 may also assist in aligning the plates 302 and 304 by drawing the plates 302 and 304 into alignment as the protrusion(s) 126 are inserted into the aperture(s) 130.

Referring to FIG. 3, the first and second plate retention mechanisms 108 and 110 of the first alignment guide 102 are illustrated. As illustrated, the first plate retention mechanism 108 includes a first pivot member 134, a first bias member, such as spring 136, and a first fastener, such as pin 138. The first pivot member 134 includes an aperture 140 defining a pivot point, a gripping portion 142 on a first side of the pivot point, a plate engaging foot 144 on a second side of the pivot point, and a stop 146 extending from the first pivot member 134 substantially at the pivot point.

The spring 136 is disposed in a channel 148 of the first body portion 106, and the aperture 140 of the first pivot member 134 is aligned with a corresponding aperture 150 of the first body portion 106. The stop 146 of the first pivot member 134 is also aligned with the channel 148 and spring 136, thereby retaining the spring 136 in the channel 148. The pin 138 is then inserted into the aperture 140 and aperture 150 to couple the first pivot member 134 to the first body portion 106. The spring 136 exerts a force on the stop 146 in a direction away from the first face 128 of the first body portion 106. This causes the foot 144 to be in a close position until the gripping portion 142 is pushed to cause the stop 146 to move against the bias force of the spring 136, thereby moving the foot 144 to an open portion, in which the first alignment guide 102 may receive a plate, such as plate 302.

The second plate retention mechanism 110 is substantially the same as the first plate retention mechanism 108. For example, the second plate retention mechanism 110 includes a second pivot member 152, a second bias member, such as spring 154, and a second fastener, such as pin 156. The second pivot member 152 includes an aperture 158 defining a pivot point, a gripping portion 160 on a first side of the pivot point, a plate engaging foot 162 on a second side of the pivot point, and a stop 164 extending from the second pivot member 152 substantially at the pivot point. The spring 154 is disposed in a channel indicated at 166 of the first body portion 106, substantially identical to that of channel 148, and the aperture 158 of the second pivot member 152 is aligned with a corresponding aperture (not shown) of the first body portion 106. The stop 164 is aligned with the channel 166 and spring 154, thereby retaining the spring 154 in the channel 166. The pin 156 is then inserted into the aperture 158 and corresponding aperture of the first body portion 106 to couple the second pivot member 152 to the first body portion 106.

Figure 4:
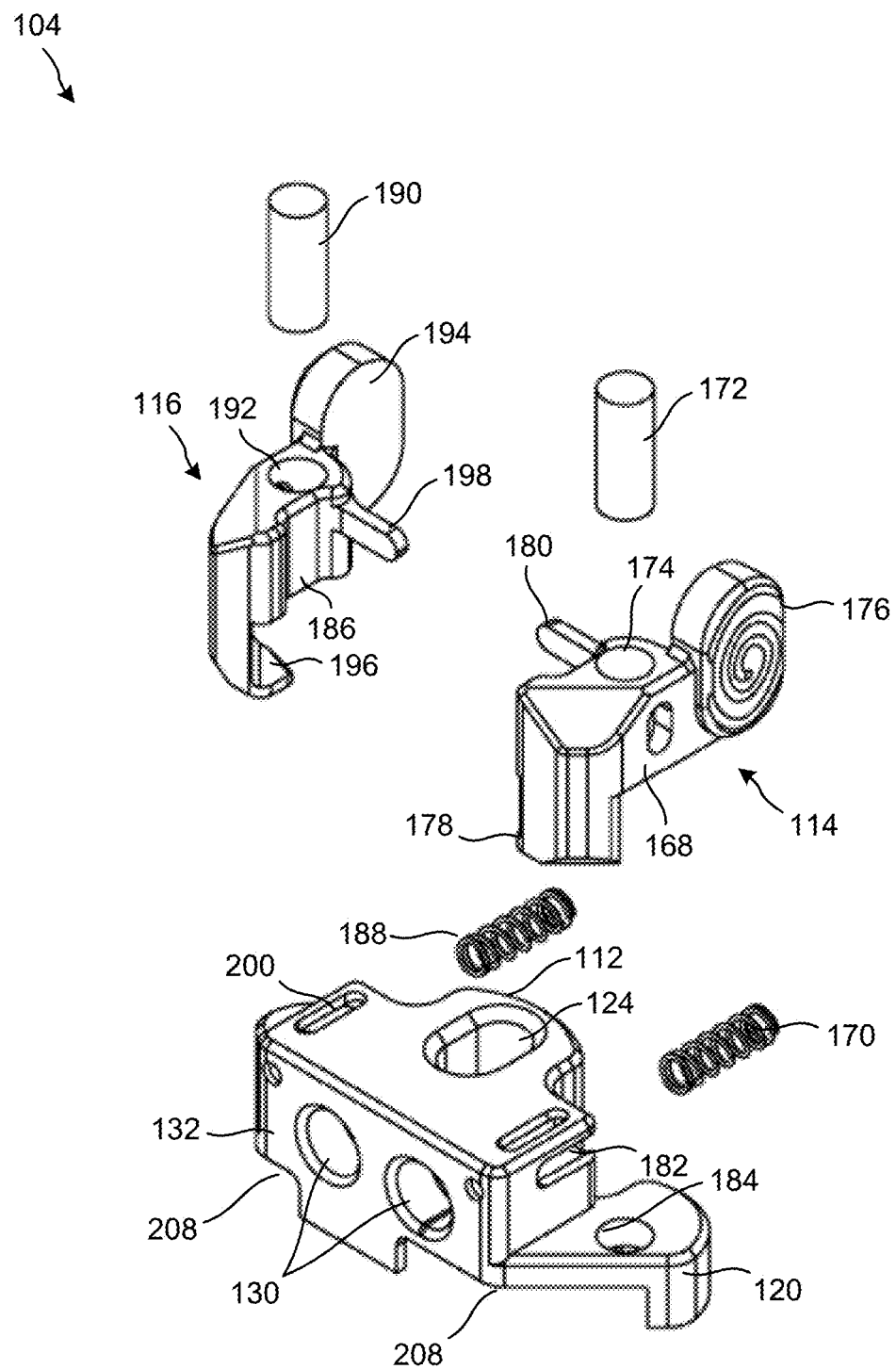

Referring to FIG. 4, the first and second plate retention mechanisms 114 and 116 of the second alignment guide 104 are illustrated. The first and second plate retention mechanisms 114 and 116 of the second alignment guide 104 are substantially the same as the first and second plate retention mechanisms 108 and 110 of the first alignment guide 102. As illustrated, the first plate retention mechanism 114 includes a first pivot member 168, a first bias member, such as spring 170, and a first fastener, such as pin 172. The first pivot member 168 includes an aperture 174 defining a pivot point, a gripping portion 176 on a first side of the pivot point, a plate engaging foot 178 on a second side of the pivot point, and a stop 180 extending from the first pivot member 168 substantially at the pivot point.

The spring 170 is disposed in a channel 182 of the second body portion 112, and the aperture 174 of the first pivot member 168 is aligned with a corresponding aperture 184 of the second body portion 112. The stop 180 is aligned with the channel 182 and spring 170, thereby retaining the spring 170 in the channel 182. The pin 172 is then inserted into the aperture 174 and aperture 184 to couple the first pivot member 168 to the second body portion 112.

Similarly, the second plate retention mechanism 116 includes a second pivot member 186, a second bias member, such as spring 188, and a second fastener, such as pin 190. The second pivot member 186 includes an aperture 192 defining a pivot point, a gripping portion 194 on a first side of the pivot point, a plate engaging foot 196 on a second side of the pivot point, and a stop 198 extending from the second pivot member 186 substantially at the pivot point. The spring 188 is disposed in a channel indicated at 200 of the second body portion 112, identical to that of channel 182, and the aperture 192 of the second pivot member 186 is aligned with a corresponding aperture (not shown) of the second body portion 112. The stop 198 is aligned with the channel 200 and spring 188, thereby retaining the spring 188 in the channel 200. The pin 190 is then inserted into the aperture 192 and corresponding aperture of the second body portion 112 to couple the second pivot member 186 to the second body portion 112.

Figure 5:
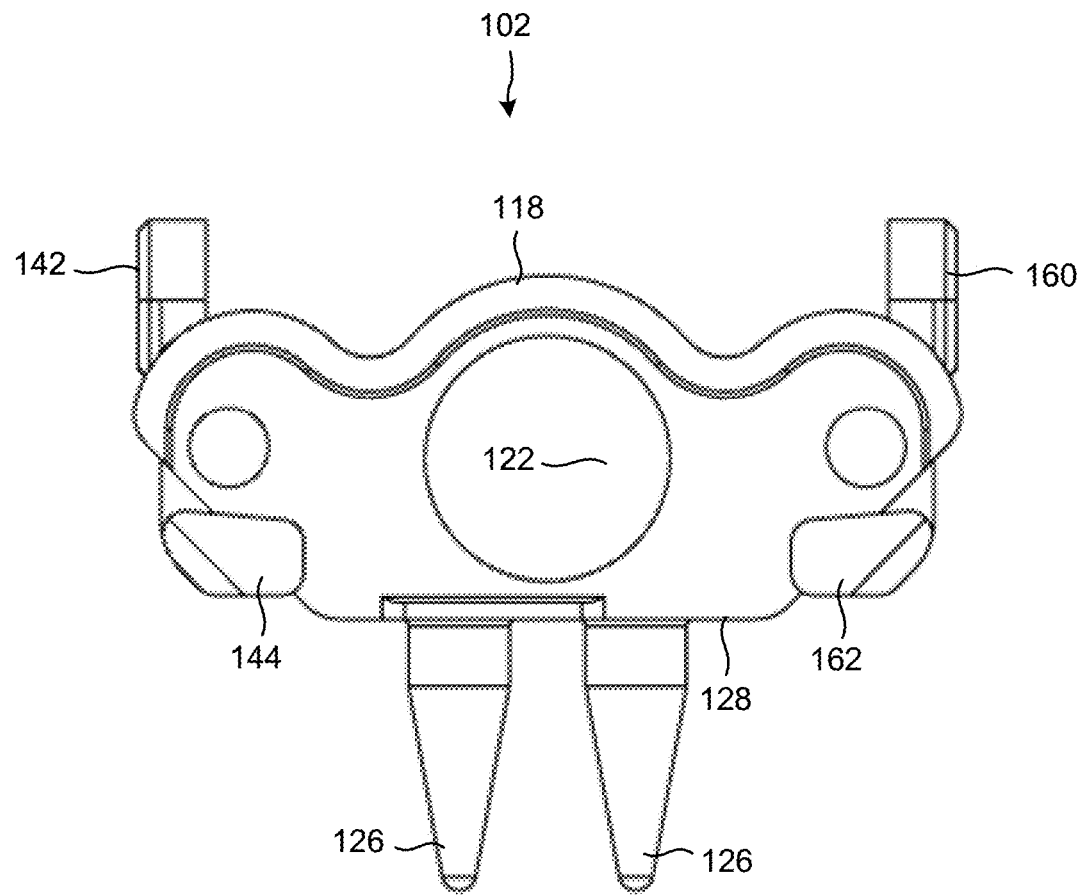
FIGS. 5-10 illustrate views of the alignment devices of FIG. 1 coupling to plates in accordance with an embodiment of the disclosure.
Figure 5:
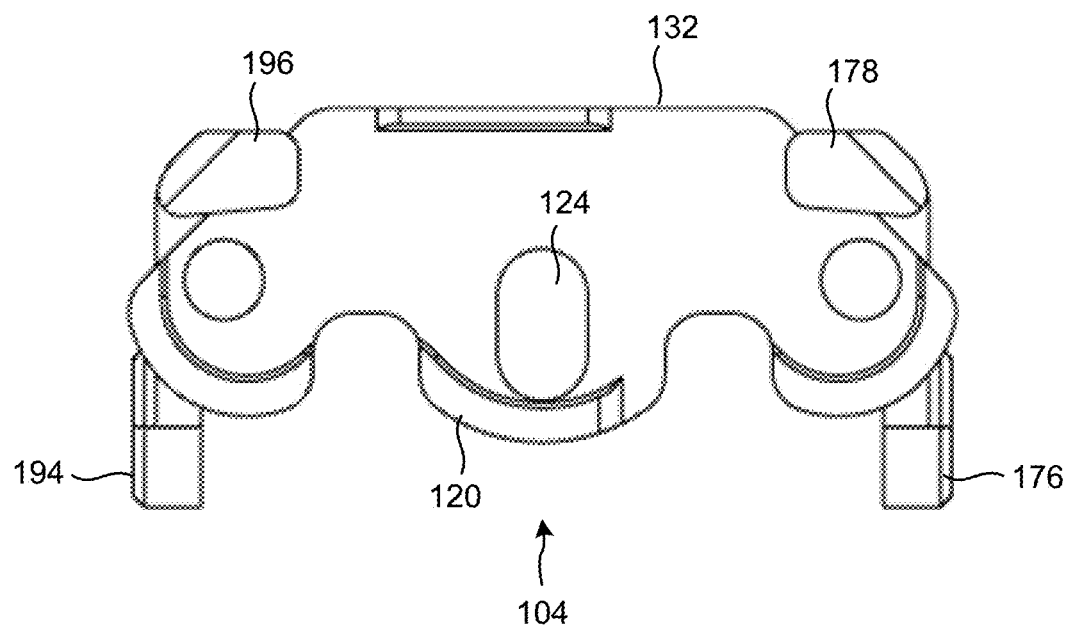
Figure 6:
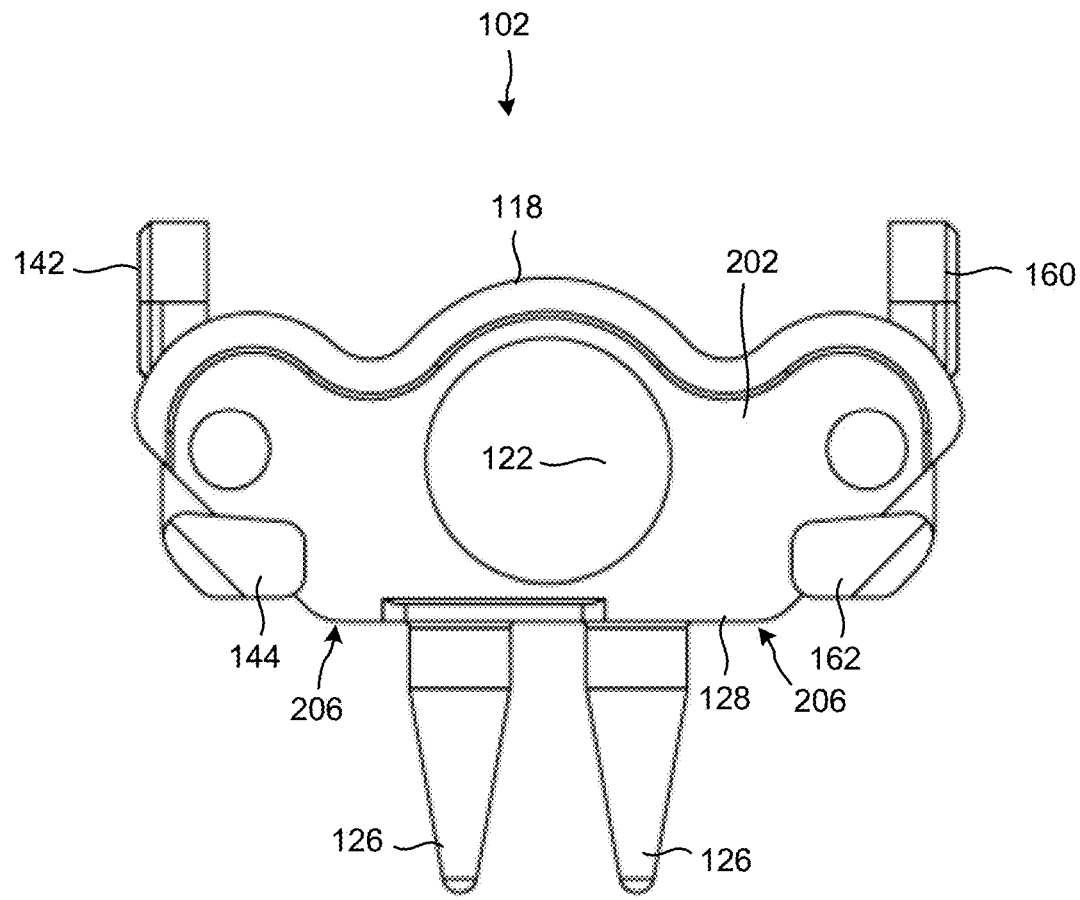
Figure 6:
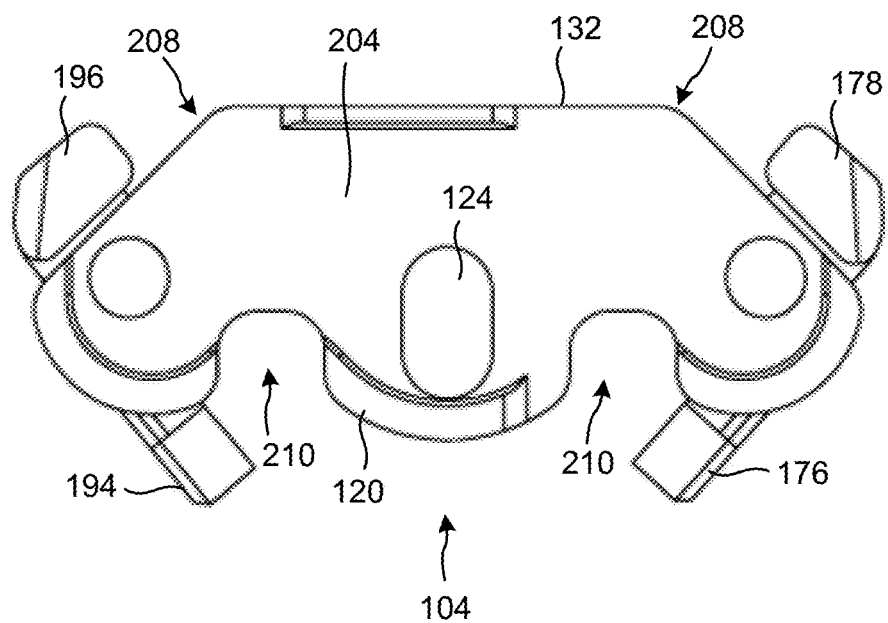

FIGS. 5-10 illustrate views of the first and second alignment guides 102 and 104, and the first and second alignment guides 102 and 104 being coupled to the corresponding plates 302 and 304. As illustrated in FIG. 5, the feet 144 and 162 of the first alignment guide 102, and the feet 178 and 196 of the second alignment guide 104 are in a closed position. This is caused by the bias force of the respective springs (136, 154, 170, and 188) and the corresponding stops (146, 164, 180, 186).

To move the feet 144 and 162 of the first alignment guide 102 to the open position, the gripping portions 142 and 160 are depressed in a direction toward one another. This causes the corresponding stops (146 and 164) to move against the spring force of the corresponding springs (136 and 154), which causes a distance between the feet 144 and 162 to increase. Similarly, to move the feet 178 and 196 of the second alignment guide 104 to the open position, the gripping portions 176 and 194 are depressed in a direction toward one another. This causes the corresponding stops (180 and 186) to move against the spring force of the corresponding springs (170 and 188), which causes a distance between the feet 178 and 196 to increase, as illustrated in FIGS. 6-9.

In the open position, the first and second alignment guides 102 and 104 may be coupled to the corresponding plates 302 and 304. For example, referring to FIGS. 6-8, the base portion 118 of the first alignment guide 102 is shaped to receive the plate 302 in recess 202 defined by the base portion 118, and the base portion 120 of the second alignment guide 104 is shaped to receive the plate 304 in recess 204 defined by the base portion 120.

As disclosed in U.S. Patent Application Publication No. 2015/0119887, entitled Orthopedic Fixation Device, System and Method, filed Oct. 27, 2014, the plates 302 and 304 may include a locking element 310 that may be coiled around the ratchet mechanism 306 to urge the plates 302 and 304 together. The plate 304 may include shear pins 312 that are received in corresponding receiving receptacles in the plate 302. Further, the plates 302 and 304 may include corresponding recesses 314 and 316 that receive the corresponding feet (144, 162, 178, 196) of the alignment guides.

Figure 7:
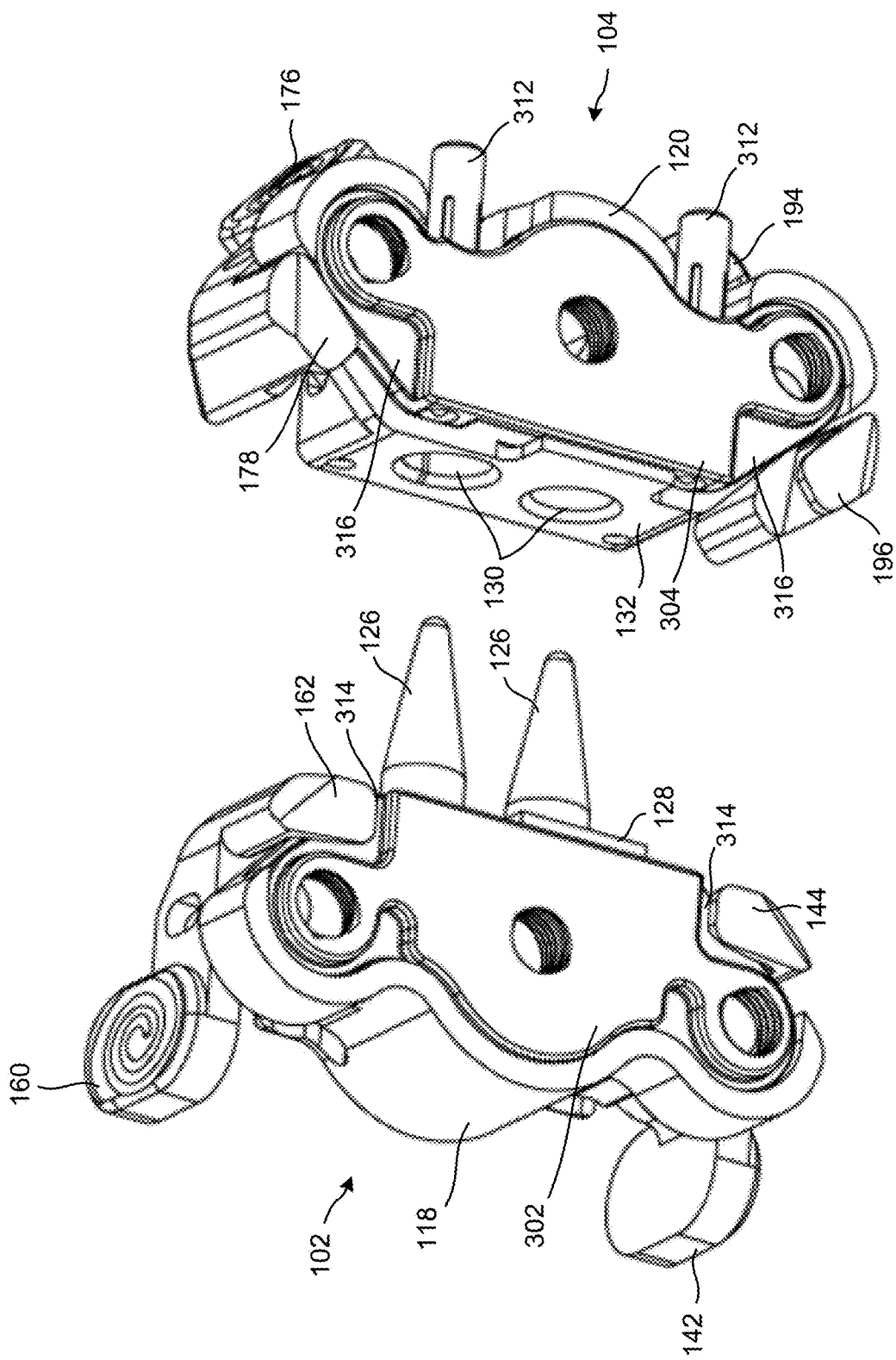
Figure 8:
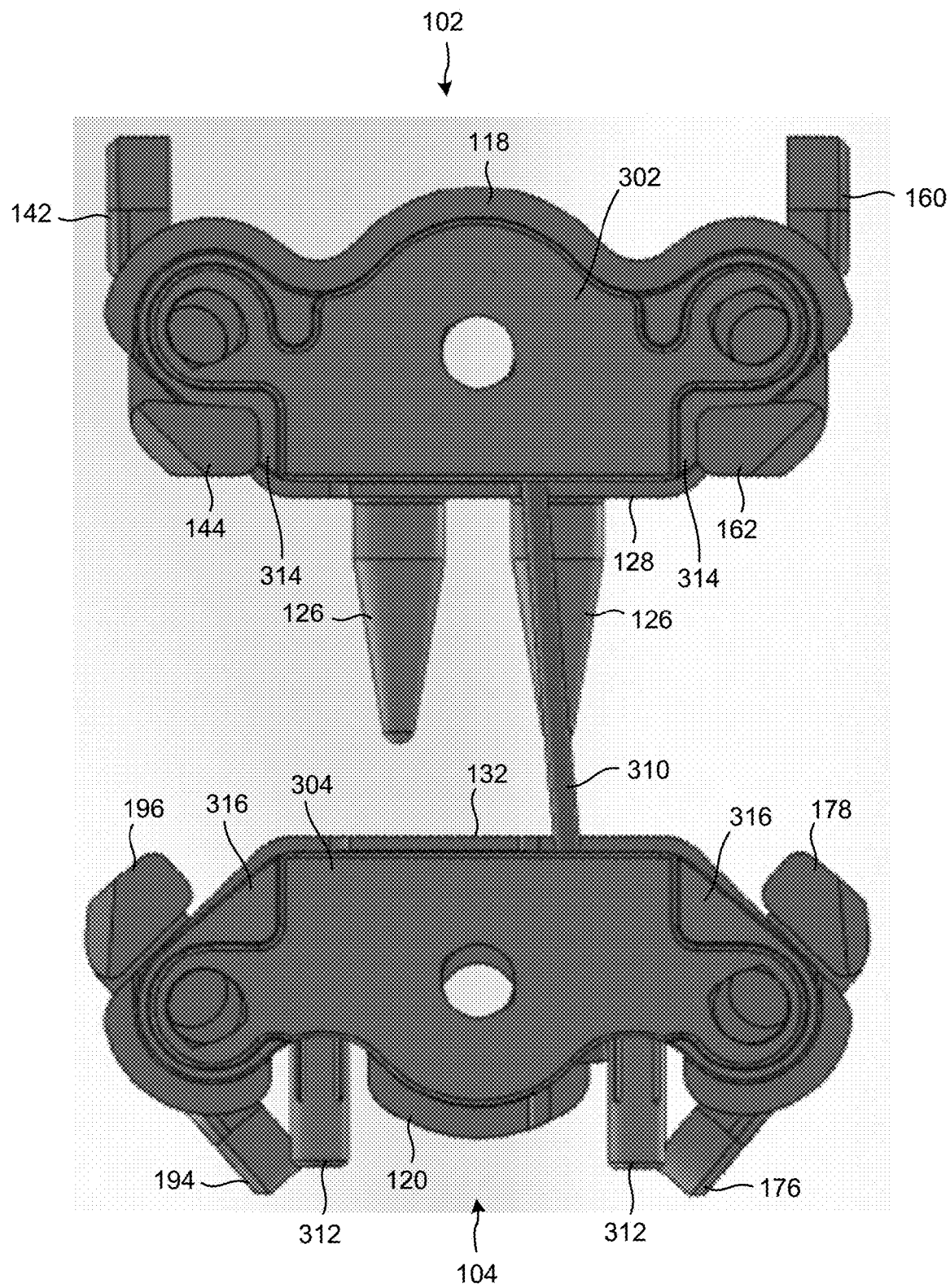
Figure 9:
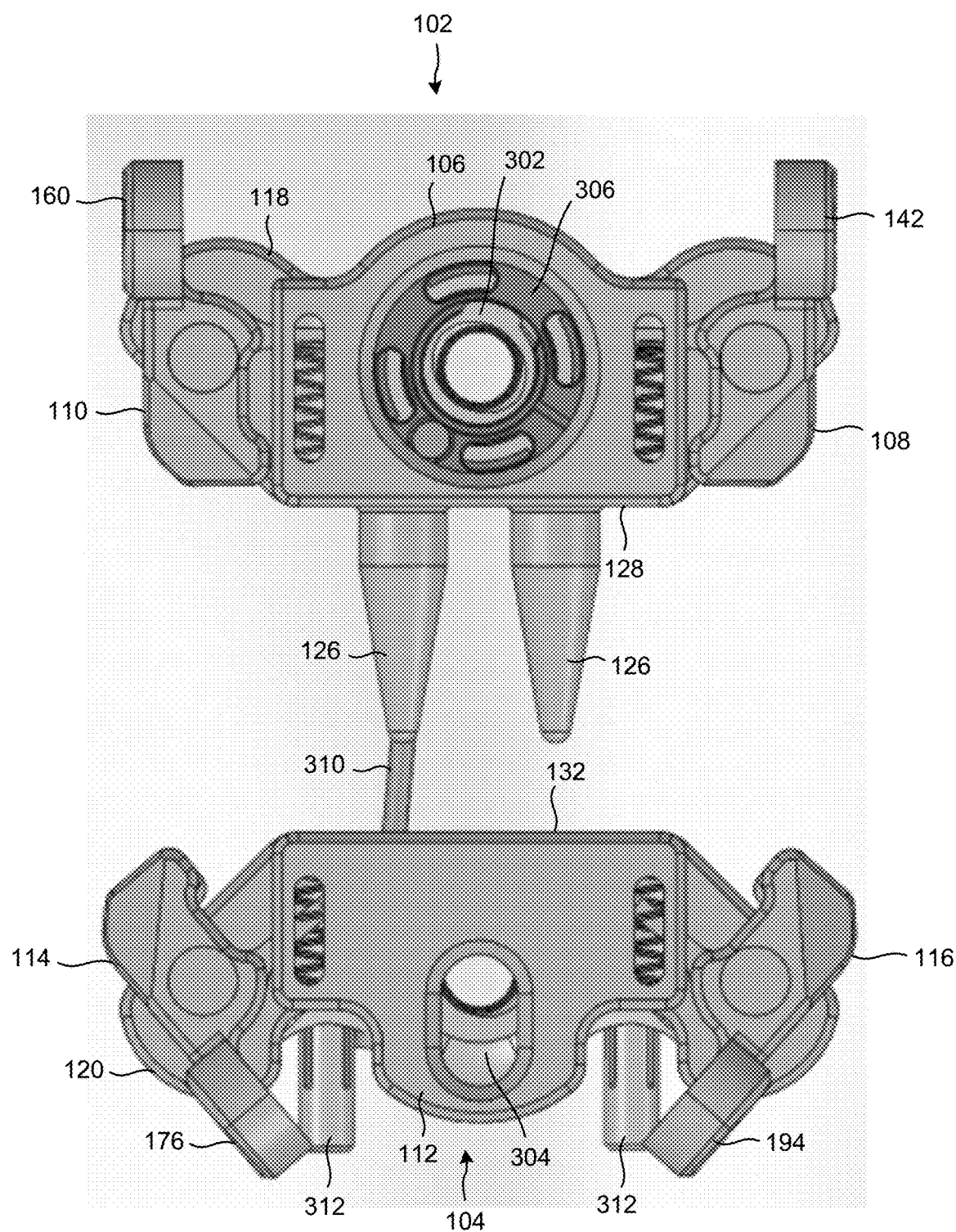

In this respect, the base portion 118 of the first alignment guide 102 may include cut-outs 206 (as best illustrated in FIG. 3) to allow for the locking element 310 to extend from the plate 302 to the plate 304 and be coiled around the ratchet mechanism 306. The cut-outs 206 in the base portion 118 may also allow for the shear pins 312 to be received in the corresponding receiving receptacles in the plate 302. Similarly, the base portion 120 of the second alignment guide 104 may include cut-outs 208 (as illustrated in FIGS. 4 and 7) to allow for the locking element 310 to extend from the plate 302 to the plate 304, and the shear pins 312 to be deployed and received in the corresponding receiving receptacles in the plate 302. The base portion 120 may also include cut-outs 210 that allow for the shear pins 312 to extend from the plate 304 in a non-deployed position (as illustrated in FIGS. 7-9). Thus, the base portion 118 of the first alignment guide 102 is shaped to receive the plate 302, and the base portion 120 of the second alignment guide 104 is shaped to receive the plate 304.

In one method of practice, the plates 302 and 304 are installed or affixed onto a bone at a predetermined distance apart with the shear pins 312 in the non-deployed position. A resection or cutting of the bone is performed between the plates 302 and 304, and a desired surgery is performed. Upon completion of the surgery, the locking element 310 is installed in the plates 302 and 304.

Figure 10:
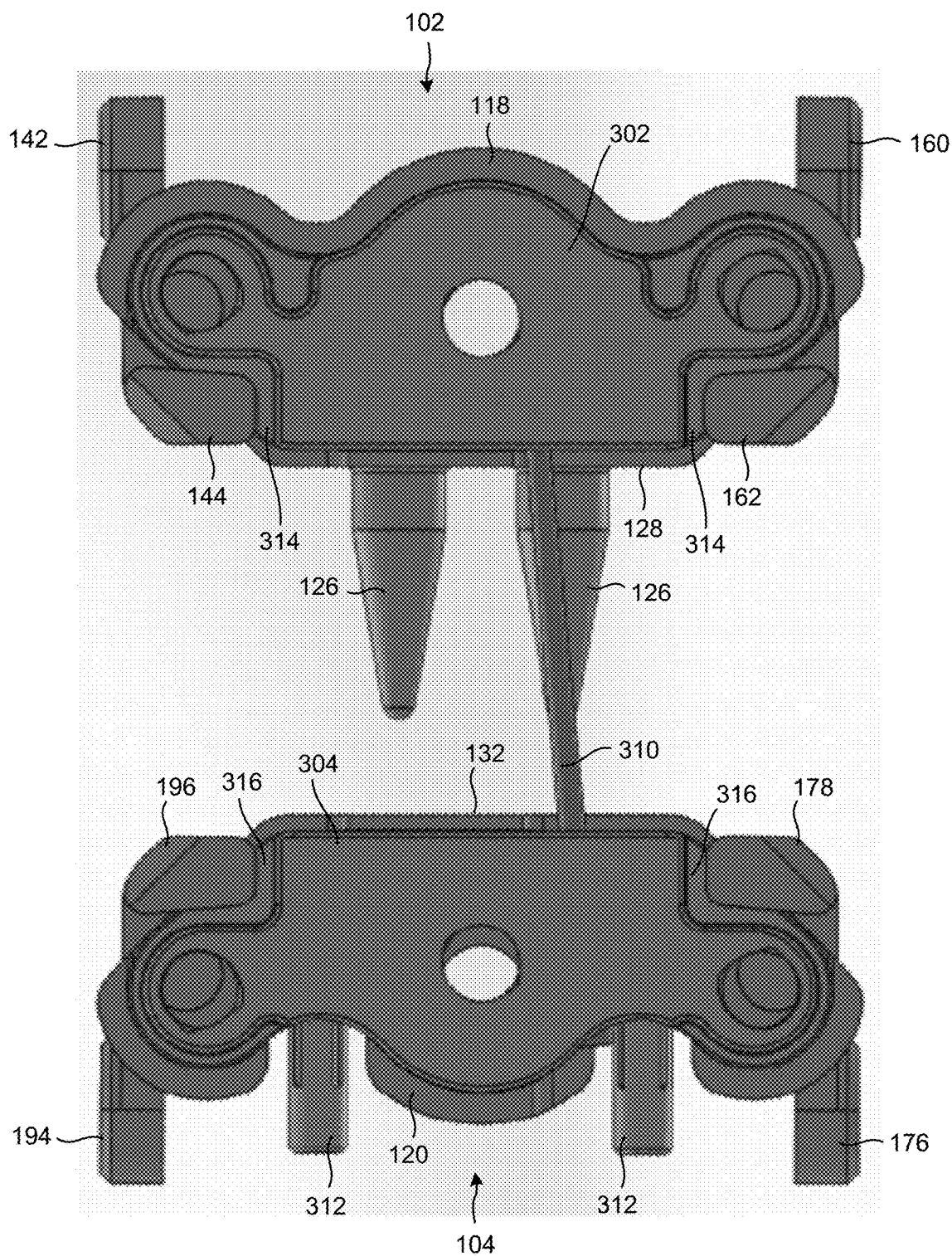
Figure 11:
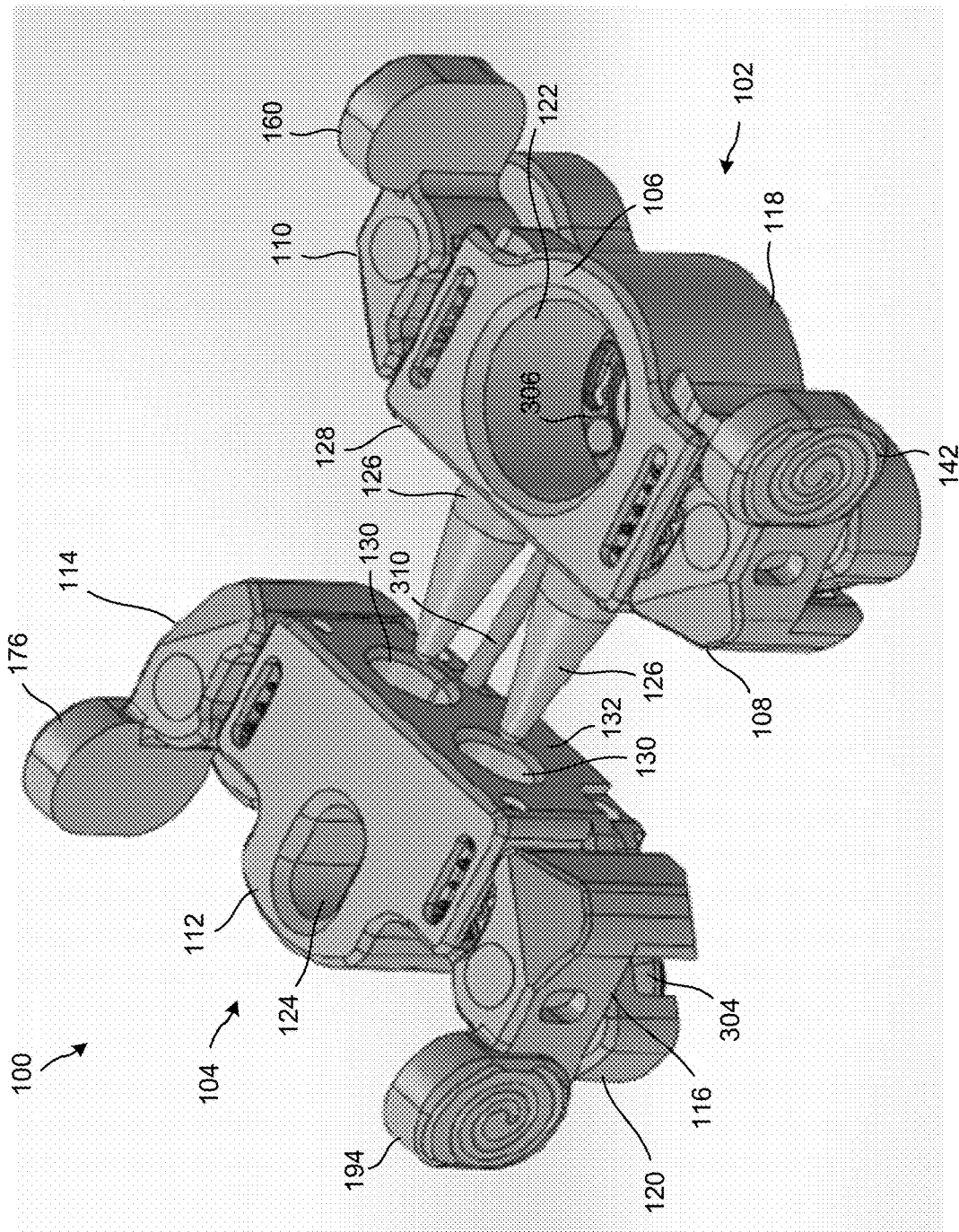
FIGS. 11-14 illustrate the alignment devices of FIG. 1 being used to align the plates in accordance with an embodiment of the disclosure.
Figure 12:
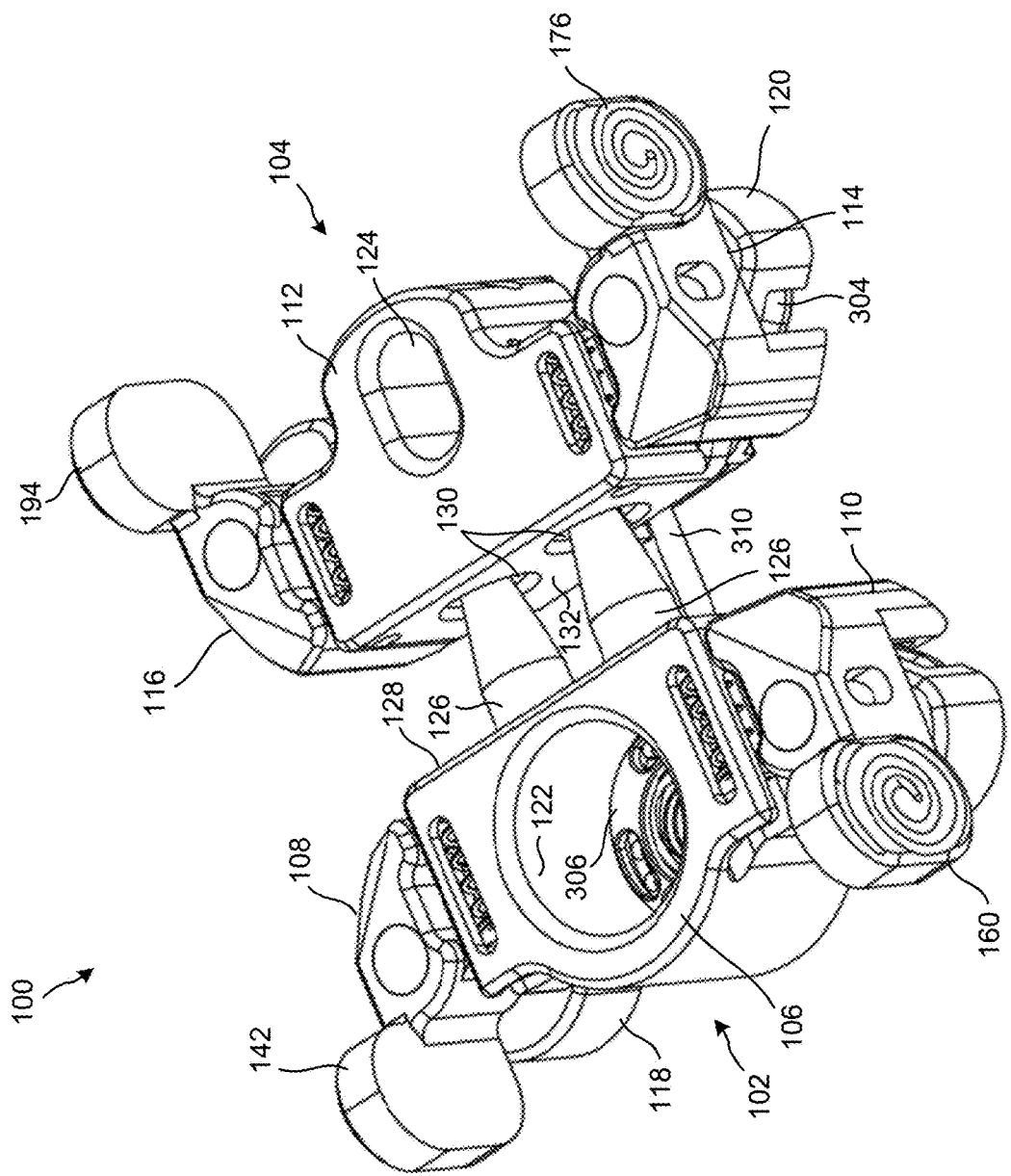

Referring to FIGS. 7, 8, and 10, the first alignment guide 102 is then coupled to the plate 302 by depressing the gripping portions 142 and 160 in a direction toward one another. This causes the corresponding stops (146 and 164) to move against the spring force of the corresponding springs (136 and 154), which causes a distance between the feet 144 and 162 to increase. The first alignment guide 102 is then placed over the plate 302 and the gripping portions 142 and 160 are released. Upon release of the gripping portions 142 and 160, the distance between the feet 144 and 162 decreases and the feet return to the closed position, thereby engaging the recesses 314 of the plate 302, as illustrated in FIG. 7-10.

Similarly, the second alignment guide 104 is coupled to the plate 304 by depressing the gripping portions 176 and 194 in a direction toward one another. This causes the corresponding stops (180 and 186) to move against the spring force of the corresponding springs (170 and 188), which causes a distance between the feet 178 and 196 to increase, as illustrated in FIGS. 7-9. The second alignment guide 104 is then placed over the plate 304 and the gripping portions 176 and 194 are released. Upon release of the gripping portions 176 and 194, the distance between the feet 178 and 196 decreases and the feet return to the closed position, thereby engaging the recesses 316 of the plate 304, as illustrated in FIG. 10.

Referring to FIGS. 11-14, once the first and second alignment guides 102 and 104 are coupled to the corresponding plates 302 and 304, the plates may be ratcheted together. For example, a ratchet tool may be inserted into the first aperture 122 of the first alignment guide 102 and engaged with the ratchet mechanism 306 of the plate 302. The tool may be used to ratchet and coil the locking mechanism 310 to cause the plates 302 and 304 to be urged together.

Figure 13:
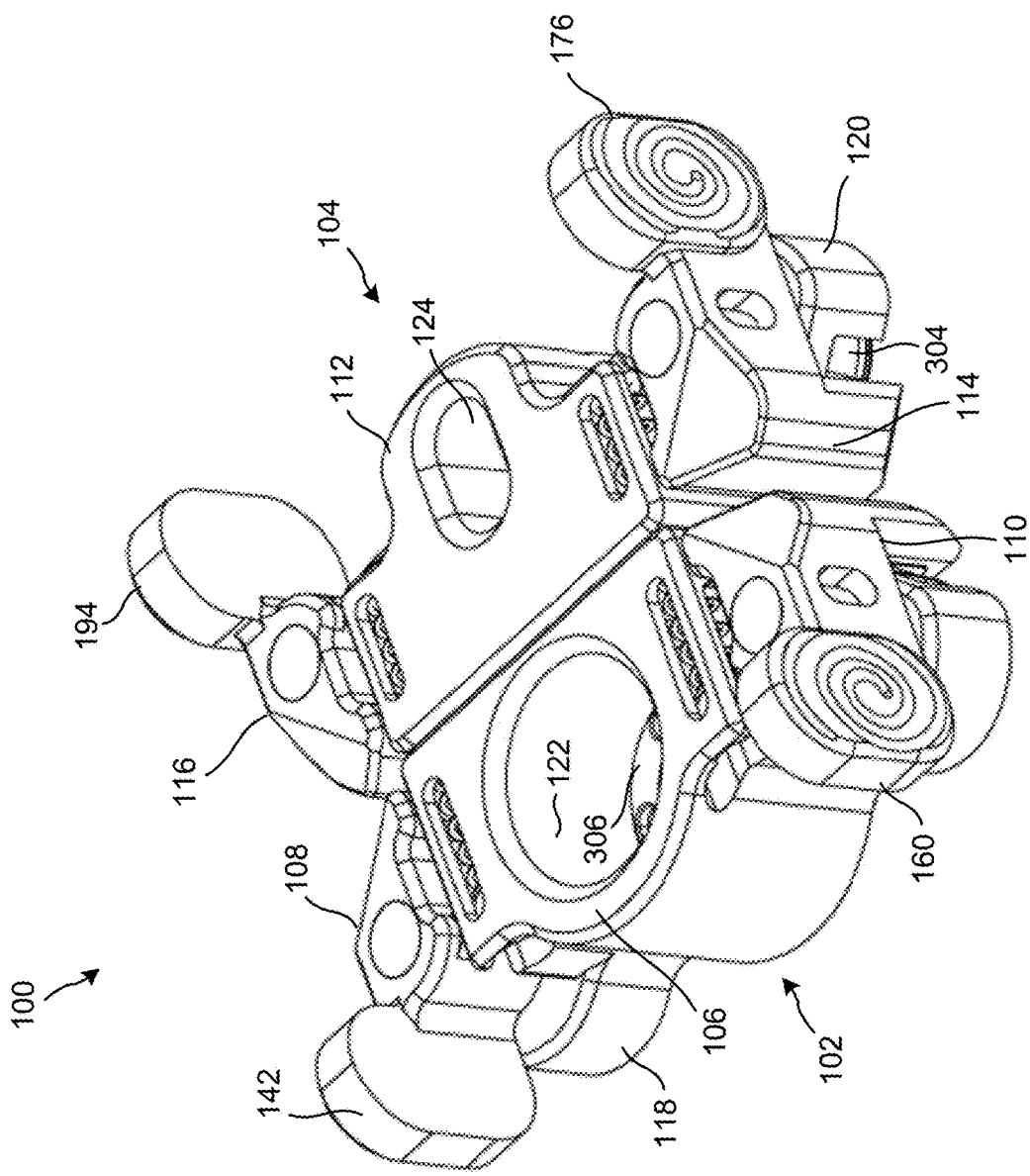
Figure 14:
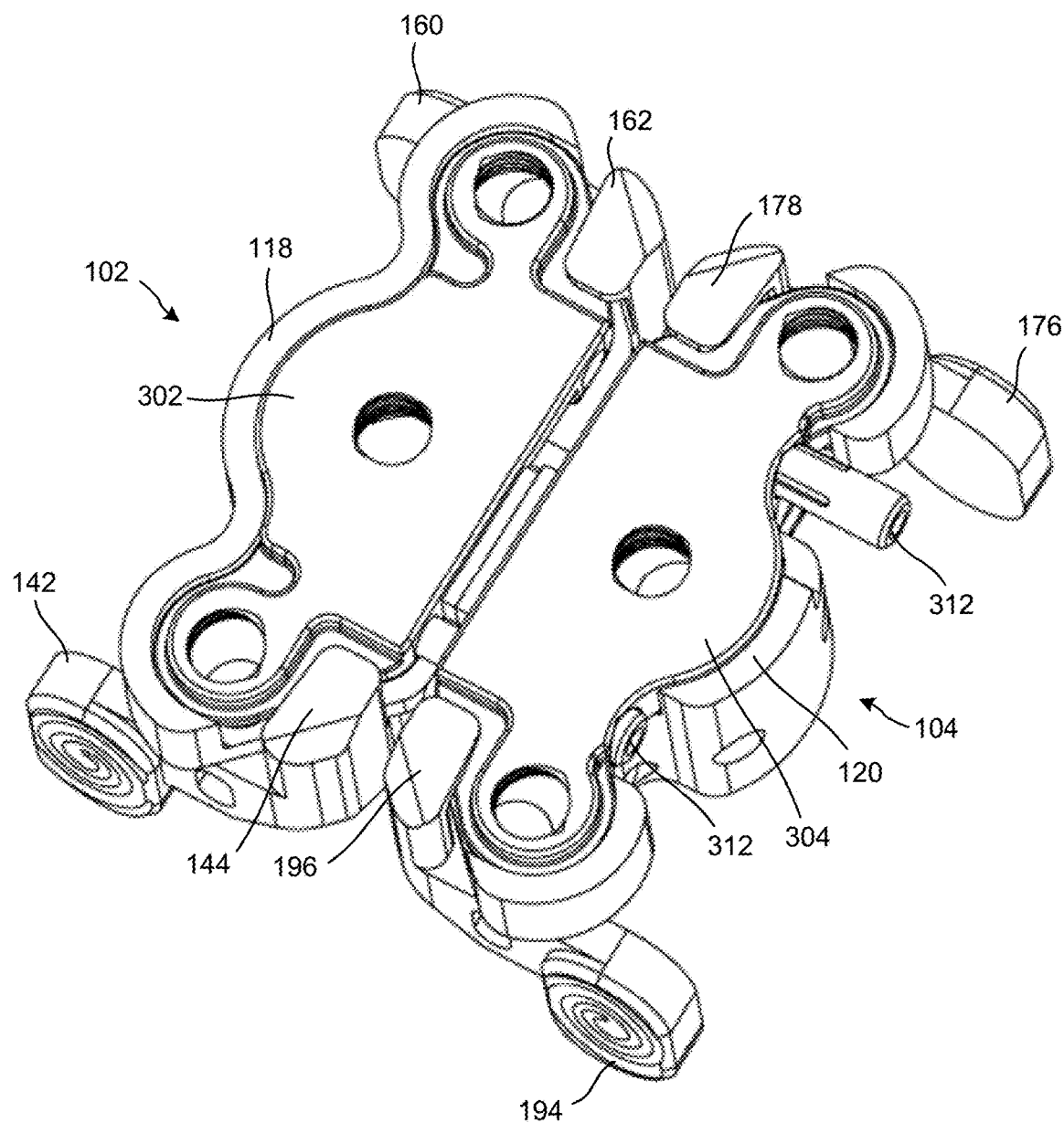

As the plates 302 and 304 are urged together, the protrusion(s) 126 of the first body portion 106 are urged closer and toward engagement with the apertures 130 in a second face 132 of the second body portion 112 until the plates 302 and 304 are aligned and the resection of the bone is closed, for example, as illustrated in FIG. 13. The shear pins 312 may then be deployed and received in corresponding receiving receptacles in the plate 302, as illustrated in FIG. 14, in which one of the shear pins 312 is deployed.

The first and second alignment guides 102 and 104 may then be removed from the corresponding plates 302 and 304. For example, the first alignment guide 102 may be released from the plate 302 by depressing the gripping portions 142 and 160 in a direction toward one another. This causes the corresponding stops (146 and 164) to move against the spring force of the corresponding springs (136 and 154), which causes a distance between the feet 144 and 162 to increase and disengage the recesses 314 of the plate 302. Similarly, the second alignment guide 104 may be released from the plate 304 by depressing the gripping portions 176 and 194 in a direction toward one another. This causes the corresponding stops (180 and 186) to move against the spring force of the corresponding springs (170 and 188), which causes a distance between the feet 178 and 196 to increase and disengage the recesses 316 of the plate 304.

In removing the first and second alignment guides 102 and 104 from the corresponding plates 302 and 304, both the first and second alignment guides 102 and 104 may be removed simultaneously, by depressing the gripping portions 142 and 160 and depressing the gripping portions 176 and 194 at a same time. This is due to the engagement of the protrusion(s) 126 with the apertures 130.

While the first and second alignment guides 102 and 104 are described above as being used to assist in aligning the corresponding plates 302 and 304 to close a resection of a bone, the first and second alignment guides 102 and 104 may also be used to assist in placing the corresponding plates 302 and 304 onto the bone. For example, the first and second alignment guides 102 and 104 may be fixed directly to the bone with fasteners prior to resection. After the bone resection(s) is made and the desired surgical procedure performed, the first and second alignment guides 102 and 104 may be used to bring the bone back to its natural anatomic position. The plates 302 and 304 may then be placed and fixed to the bone to establish ridged fixation.

The one or more protrusions 126 of the first body portion 106 may also be retractable. This allows the first and second alignment guides 102 and 104 to be placed onto the bone, pre-resection, and a resection or cutting of the bone to be performed between the first and second alignment guides 102 and 104. In this manner, the one or more protrusions 126 may be extended from the first body portion 106 while the first and second alignment guides 102 and 104 are coupled or fixed to the bone, and may be retracted to allow clearance for the resection or cutting of the bone to be performed between the first and second alignment guides 102 and 104.

The alignment guides 102 and 104 may also include one or more apertures that communicate with internal components and moving elements of the corresponding alignment guides 102 and 104. This allows for the alignment guides 102 and 104 to be easily cleaned, sterilized, and reused. The alignment guides 102 and 104 may be adapted or modified to accommodate different plate geometries and features. The alignment guides 102 and 104 may be used in conjunction with any type of bone plate or other type of plate. For example, the alignment guides 102 and 104 may be used for alignment and fixation of boney elements to prevent motion in a particular direction as well as providing dynamic stabilization. The alignment guides 102 and 104 may also be used prior to or after a separation of a bone or other calcaneus body parts to align one or more plates.

The alignment guides 102 and 104 may also be wholly or partially transparent to allow the user to view the progress of the plates being drawn together and into alignment. The fasteners used to couple the pivot member to the body portions may also be any type of fastener, including, pins, rivets, screws, etc.

Although the devices, systems, and methods have been described and illustrated in connection with certain embodiments, many variations and modifications should be evident to those skilled in the art and may be made without departing from the spirit and scope of the disclosure. The disclosure is thus not to be limited to the precise details of methodology or construction set forth above as such variations and modification are intended to be included within the scope of the disclosure.

What is claimed is:

1. A system for guiding alignment of fixation devices, comprising:
    a first alignment guide including a first retention mechanism adapted to couple the first alignment guide to a first fixation device on a first side of a cut body part, and a protrusion having a conical shape that extends from a first face of the first alignment guide; and
    a second alignment guide including a second retention mechanism adapted to couple the second alignment guide to a second fixation device on a second side of the cut body part, and an alignment aperture in a second face of the second alignment guide adapted to receive the protrusion, wherein the first and second alignment guides assist in aligning the first fixation device with the second fixation device to close the cut body part.

2. The system of claim 1, wherein the first alignment guide includes an aperture extending substantially vertically through the first alignment guide and adapted to align with a ratchet mechanism of the first fixation device.

3. The system of claim 1, wherein the second alignment guide includes an aperture extending substantially vertically through the second alignment guide and adapted to align with a fastener of the second fixation device.

4. The system of claim 1, wherein the first retention mechanism includes:
    a pivot member pivotably coupled to a body of the first alignment guide;
    a bias member adapted to bias the pivot member to a closed position; and
    an engagement member adapted to engage the first fixation device when the pivot member is in the closed position.

5. The system of claim 1, wherein
    the protrusion includes first and second protrusions extending from-the first face of the first alignment guide; and
    the alignment aperture includes first and second alignment apertures in the second face of the second alignment guide adapted to respectively receive the first and second protrusions.

6. The system of claim 1, wherein the conical shape has a cross sectional area that decreases as the protrusion extends away from the first face.

7. The system of claim 1, wherein the second retention mechanism includes:
    a pivot member pivotably coupled to a body of the second alignment guide;
    a bias member adapted to bias the pivot member to a closed position; and
    an engagement member adapted to engage the second fixation device when the pivot member is in the closed position.

8. A device for guiding alignment of a fixation device, comprising:
    a body portion;
    a protrusion having a conical shape that extends from a face of the body portion, and that is adapted to engage an aperture of second device; and
    a retention mechanism including a pivot member pivotably coupled to the body portion and having an engagement member adapted to engage a first fixation device when the pivot member is in a closed position, and couple the device to the first fixation device on a first side of a cut body part.

9. The device of claim 8, further comprising an aperture extending substantially vertically through the body portion.

10. The device of claim 8, further comprising a bias member disposed in the body portion and adapted to bias the pivot member to the closed position.

11. The device of claim 8, wherein the protrusion includes first and second protrusions.

12. A device for guiding and aligning two pieces of a fixation device, comprising:
    a first guide having a first pair of gripping elements movably coupled to the first guide and adapted to be movable between a first open position and a first closed position, in the first closed position, the first pair of gripping elements being adapted to releasably hold a first piece of the fixation device, wherein the first guide includes a protrusion having a conical shape that extends from a first face of the first guide; and
    a second guide having a second pair of gripping elements movably coupled to the second guide and adapted to be movable between a second open position and a second closed position, in the second closed position, the second pair of gripping elements being adapted to releasably hold a second piece of the fixation device, the first and second guides are adapted to interconnect with one another to bring the first and second pieces of the fixation device into alignment.

13. The device of claim 12, wherein the protrusion includes first and second protrusions extending from the first face of the first guide.

14. The device of claim 12, wherein the conical shape has a cross sectional area that decreases as the protrusion extends away from the first face.

15. The device of claim 12, wherein the first pair of gripping elements includes:
- a first pivot member pivotably coupled to a first end of the first guide and having a first engagement member adapted to hold the first piece; and
- a second pivot member pivotably coupled to a second end of the first guide and having a second engagement member adapted to hold the first piece.

16. The device of claim 12, wherein the second guide includes an aperture in a second face of the second guide adapted to receive the protrusion to interconnect the first and second guides and bring the first and second pieces of the fixation device into alignment.

17. The device of claim 16, wherein the second pair of gripping elements includes:
- a first pivot member pivotably coupled to a first end of the second guide and having a first engagement member adapted to hold the second piece; and
- a second pivot member pivotably coupled to a second end of the second guide and having a second engagement member adapted to hold the second piece.

18. The device of claim 12, wherein the first guide includes a first recess adapted to receive the first piece of the fixation device, and the second guide includes a second recess adapted to receive the second piece of the fixation device.

* * * * *